United States Patent [19]
Wickham

[11] Patent Number: 5,891,171
[45] Date of Patent: Apr. 6, 1999

[54] APPARATUS WITH NOISE CLASSIFICATION IN AN IMPLANTABLE CARDIAC DEVICE BY USING AN AMPLIFIER WITH A VARIABLE THRESHOLD

[75] Inventor: John Wickham, Fivedock, Australia

[73] Assignee: Pacesetter Incorporated, Sylmar, Calif.

[21] Appl. No.: 955,540

[22] Filed: Oct. 22, 1997

[51] Int. Cl.[6] .................................................. A61N 1/362
[52] U.S. Cl. .................................. 607/4; 607/9; 128/901
[58] Field of Search .................................. 607/9, 11, 14, 607/2, 4, 5, 7; 128/901; 600/509, 521

[56] References Cited

U.S. PATENT DOCUMENTS

| | | |
|---|---|---|
| 4,173,230 | 11/1979 | Digby . |
| 4,694,931 | 9/1987 | Sibertin-Blanc et al. . |
| 4,779,617 | 10/1988 | Whigham .............................. 600/509 |
| 5,048,521 | 9/1991 | Pless et al. . |
| 5,111,816 | 5/1992 | Pless et al. . |
| 5,395,393 | 3/1995 | Wickham . |
| 5,564,430 | 10/1996 | Jacobson et al. ........................ 600/510 |
| 5,755,738 | 5/1998 | Kim et al. ................................... 607/9 |
| 5,766,227 | 6/1998 | Nappholz et al. ........................... 607/9 |

*Primary Examiner*—William E. Kamm
*Assistant Examiner*—Kennedy J. Schaetzle
*Attorney, Agent, or Firm*—Gottlieb, Rackman & Reisman, P.C.

[57] ABSTRACT

An implantable cardiac device includes electrodes for sensing and pacing the heart, and optionally, defibrillation electrodes. The IECG with a noise component sensed in the heart is processed to derive raw sense signals indicative of whether the sensed QRS complexe's range is outside a certain range. This range is dynamically adjusted to compensate for the noise component. Preferably this range is defined by a threshold signal generator which generates a threshold signal including a first part which varies dynamically in accordance with a preset criteria and a second part which is at least equal to the peak amplitude of the noise.

12 Claims, 7 Drawing Sheets

APPARATUS WITH NOISE CLASSIFICATION IN AN IMPLANTABLE CARDIAC DEVICE BY USING AN AMPLIFIER WITH A VARIABLE THRESHOLD

BACKGROUND OF THE INVENTION

A. Field of Invention

This invention pertains to implantable cardiac devices (ICDs) such as pacemakers, and more particularly to such devices with means for distinguishing ambient electronic noise from arrhythmic cardiac behavior such as abnormally fast heart beats so as to provide appropriate and reliable therapy to a patient even in the presence of low level continuous noise, caused for example by electrical interference.

B. Description of the Prior Art

Typically ICDs monitor a patient's heart condition by sensing the Intra Cardiac Electrogram (IECG), a voltage that occurs when the cardiac muscle depolarizes at the beginning of each heart contraction. The IECG is sensed by one or two electrodes placed in or near the heart, where it appears as a voltage waveform which is normally referred to as the QRS complex. The IECG QRS complex during normal heart beats has an amplitude of about 15 to 25 mV and a broad frequency spectrum in the range of about 40 to 70 Hz. There are numerous systems in the prior art that detect the QRS complex by amplifying the IECG signal, filtering it to reduce noise and then detecting the QRS complex with an amplitude threshold detector. The threshold detector may have a fixed threshold or adapt the threshold to the changing amplitude of the signal.

A problem with this method of detecting cardiac activity is that because of its low amplitude and particular spectral characteristics, the IECG can be corrupted by ambient signals such as noise or artefact from natural and artificial sources. Common sources of such ambient signals include electromyographic noise from skeletal muscles near the electrodes, contact noise from intermittent contact in the electrode circuit (either the electrode wiring or between the electrode and heart muscle as the heart moves) and radiated or induced voltages from voltage lines and other external power sources. These ambient signals appear as waveforms with an amplitude and frequency content similar to the QRS complex and thus may confuse the sensing system of the ICD and cause incorrect therapy to be applied to the patient. This problem is compounded by the nature of the IECG of some arrhythmias, in particular, ventricular fibrillation, which has a lower amplitude (0.2 to 5 mv), higher rate (300 to 400 beats/min.) and lower frequency content than the normal IECG.

A common method used in many pacemakers to resolve this problem is referred to as the noise sensing window. This method takes advantage of the fact that even the fastest natural heart rates result in signals which follow a QRS complex by at least 300–400 ms. Accordingly, a noise window is designated as a window typically 100–120 ms after a QRS complex is sensed. Any signals sensed in this window are assumed to be noise.

A variation of this method is described in U.S. Pat. No. 4,173,230 to Digby entitled "Noise Elimination and Refractory Period Control In Demand Pacemakers" where a combination of filters and refractory periods are used to reduce the effect of noise.

Another noise detection method is described in U.S. Pat. No. 4,694,931 to Beck entitled "Sampled Data Sense Amplifier." The device disclosed therein searches for discontinuities in the background level of the sensed signal, and therefore ignores any noise if it is continuous and uniform.

U.S. Pat. No. 5,395,393 discloses a noise elimination method using variable amplifier thresholds.

These prior art noise detection systems have inherent problems of their own. One such problem exists if the noise level is near the detection threshold, or is of variable amplitude. In this situation, the detection is intermittent, thus providing a variable classification of noise that may lead to intermittent or indeterminate delivery of therapy to the patient. Additionally, these systems fail to work effectively when used for arrhythmia detection where an arrhythmia maybe of sufficiently high rate to cause a valid detection to fall in the noise window.

The problem of these systems misclassifying ventricular fibrillation (VF) as noise is significant. This is because the IECG for VF is highly variable and can have short intervals that have very similar characteristics to sine waves induced of by conventional power lines. This is of major consequence to patients with ICDs which require fast and accurate diagnosis of VF for the ICD to effectively save their lives from this lethal arrhythmia.

Other schemes among automatic sensing threshold, such as for example in my co-pending U.S. application Ser. No. 700,730 filed Aug. 13, 1996, entitled APPARATUS AND METHOD OF NOISE CLASSIFICATION IN AN IMPLANTABLE CARDIAC DEVICE, now U.S. Pat. No. 5,702,495. However, these schemes are very sensitive to noise at low heart rate. Moreover, these schemes are also very sensitive to noise during the asystole.

Some implantable cardiac devices are shown in U.S. Pat. No. 5,048,521 and 5,111,816.

OBJECTIVES AND SUMMARY OF THE INVENTION

It is an object of the present invention to provide a pacemaker with means for reliably detecting noise having a low amplitude before said noise is interpreted erroneously as a tachycardia.

It is another objective of the present invention to provide reliable recognition of an IECG signal even is contaminated with low level noise by a method that is not affected by (independent of) high heart rates.

Furthermore, an important objective of the invention is to present an implantable cardiac device which automatically adjusts its sensitivity during IECG detection to the ambient noise level.

It is a further objective of this invention to add features to the QRS detection system that allow the presence of these interferences to be identified reliably so that the implant may deliver correct therapy to the patient in the presence of this interference.

Other objectives and advantages of the invention shall become apparent from the following description. This invention is preferably incorporated into an ICD having threshold sensing systems that automatically adjust the threshold to adapt to different signal amplitudes, for example as disclosed in U.S. Pat. No. 5,395,393. More particularly, an ICD constructed in accordance with this invention includes means for sensing cardiac activity in a patient's heart to generate an input signal, said input signal having a noise component, means for defining a range for the input signal, and means for automatically adjusting said range to compensate for said low level noise based on a feature of the noise component.

More particularly, a feature of the noise component, such as its peak amplitude, is automatically extracted and used to generate a threshold correction factor therefrom. Preferably, this correction factor includes a safety offset to insure against abnormally high noise excursions.

DETAILED DESCRIPTION OF THE INVENTION

Figure 1:
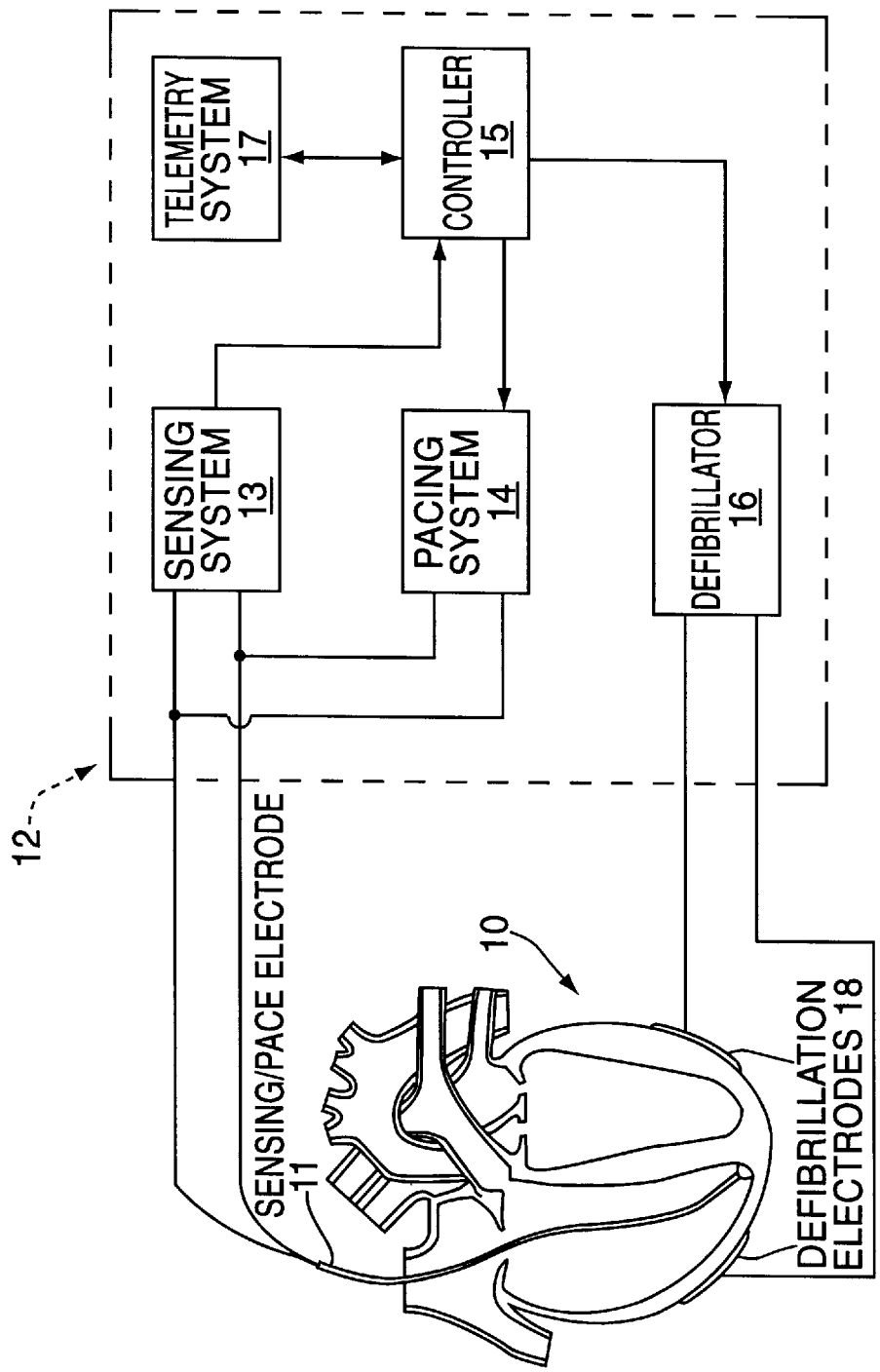
FIG. 1 is a block diagram of an arrhythmia control system in an ICD constructed in accordance with the present invention.

Referring to FIG. 1, there is depicted a block diagram of an ICD device 12 constructed in accordance with this invention which comprises a cardiac sense/pace leads 11 connected to the patient's heart 10. The intracardiac electrogram signal (IECG) sensed on one of the leads 11 is processed by the sensing system 13 to identify valid cardiac contractions. The sensing system 13 is further adapted to sense when the IECG is noisy, as described in more detail below.

A controller 15 analyzes the signals from the sensing system 13 to derive the patient's heart rate. The controller 15 compares this heart rate with criteria selected by the physician to decide whether the heart is experiencing a normal sinus rhythm (NSR), ventricular tachycardia (VT) or ventricular fibrillation (VF). Depending on this determination, the controller 15 can automatically decide whether the patient's heart is in arrhythmia and if so, select an appropriate therapy. For therapy, the controller causes either conventional cardiac pacing pulses to be delivered to the heart from the pacing system 14 and the sense/pace leads 11, or deliver cardioversion or defibrillation shock therapy via the leads 11 or a defibrillator system 16 and the defibrillation electrodes 18. The ICD device 12 can be interrogated and adjusted via the telemetry system 17. The sensing system 13 provides an indication about whether a particular sensed waveform is a valid waveform, by analyzing its shape. Moreover, sequential waveforms are further analyzed by the sensing system 13 to identify noise on the electrodes 11. The controller 15 uses this information to reject waveforms which are invalid because of their shape, or have been identified as noise.

Figure 2:
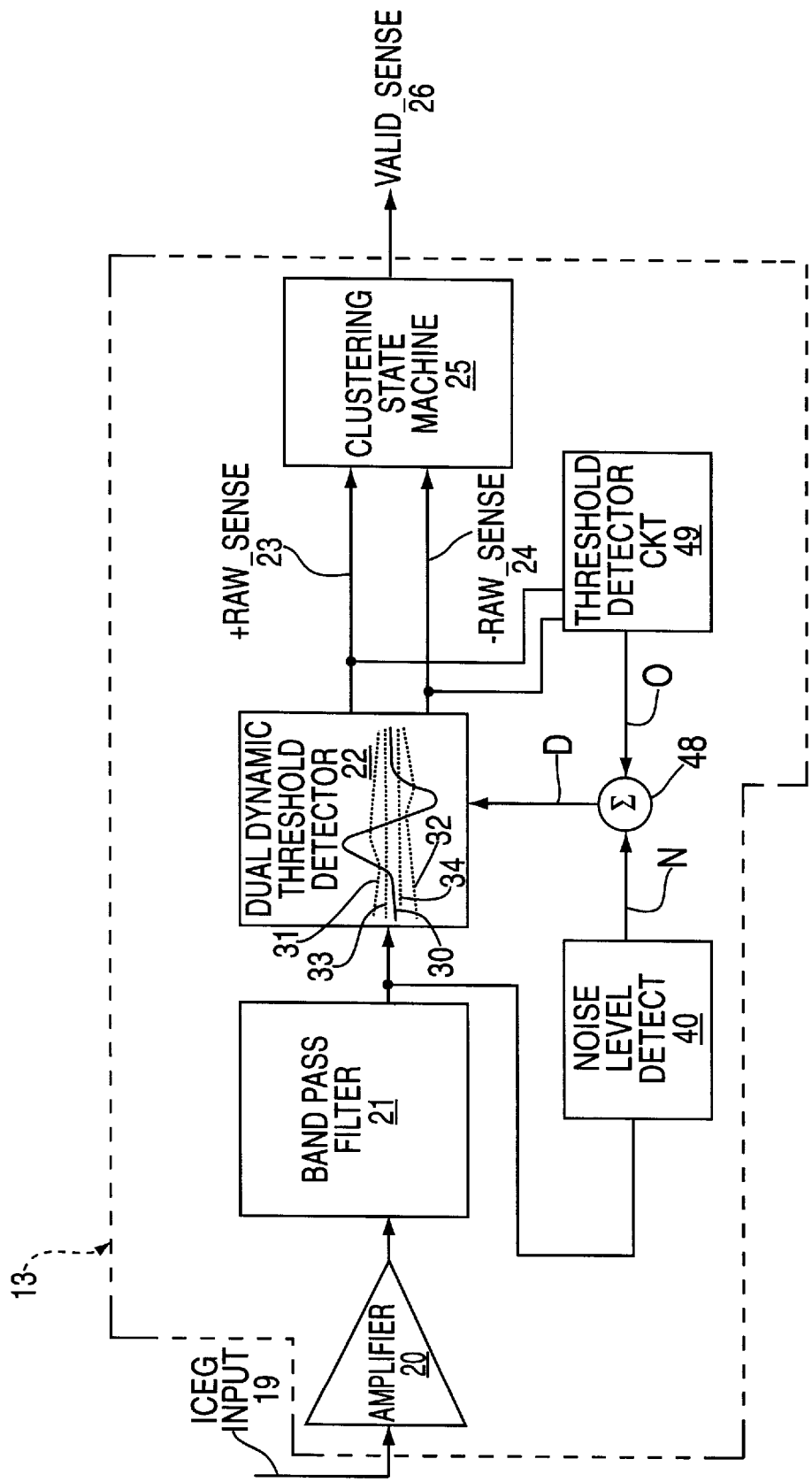
FIG. 2 is a block diagram of the sensing system of FIG. 1.

Referring to FIG. 2, there is shown a block diagram of the sensing system 13 of FIG. 1 which comprises an amplifier 20 which amplifies the IECG received on input 19 to an appropriate level for the following stages. The amplified signal is then passed through a band pass filter 21 to remove high and low frequency noise and artefacts. The filtered QRS input signal 30 is passed to a dual dynamic threshold detector 22. This detector 22 has two independent voltage thresholds and produces a digital "+Raw-sense" output 23 when the signal is greater than a positive threshold, and a −Raw-sense 24 output when the signal is less than a negative threshold.

The +Raw-sense and −Raw-sense signals are passed to a clustering state machine 25 for rationalization. The sampling rate of the system is selected so that typically, each QRS complex in the IECG is represented by between 2 and 10 raw samples. The clustering state machine 25 analyzes these samples and produces a valid-sense (26) output per heart beat if it finds the QRS complex acceptable, as discussed more fully below.

The dynamic threshold detector 22, in accordance with this invention, also takes in consideration the noise level as provided by a noise level detector 40 and adjusts the thresholds accordingly, as described below.

Figure 3:
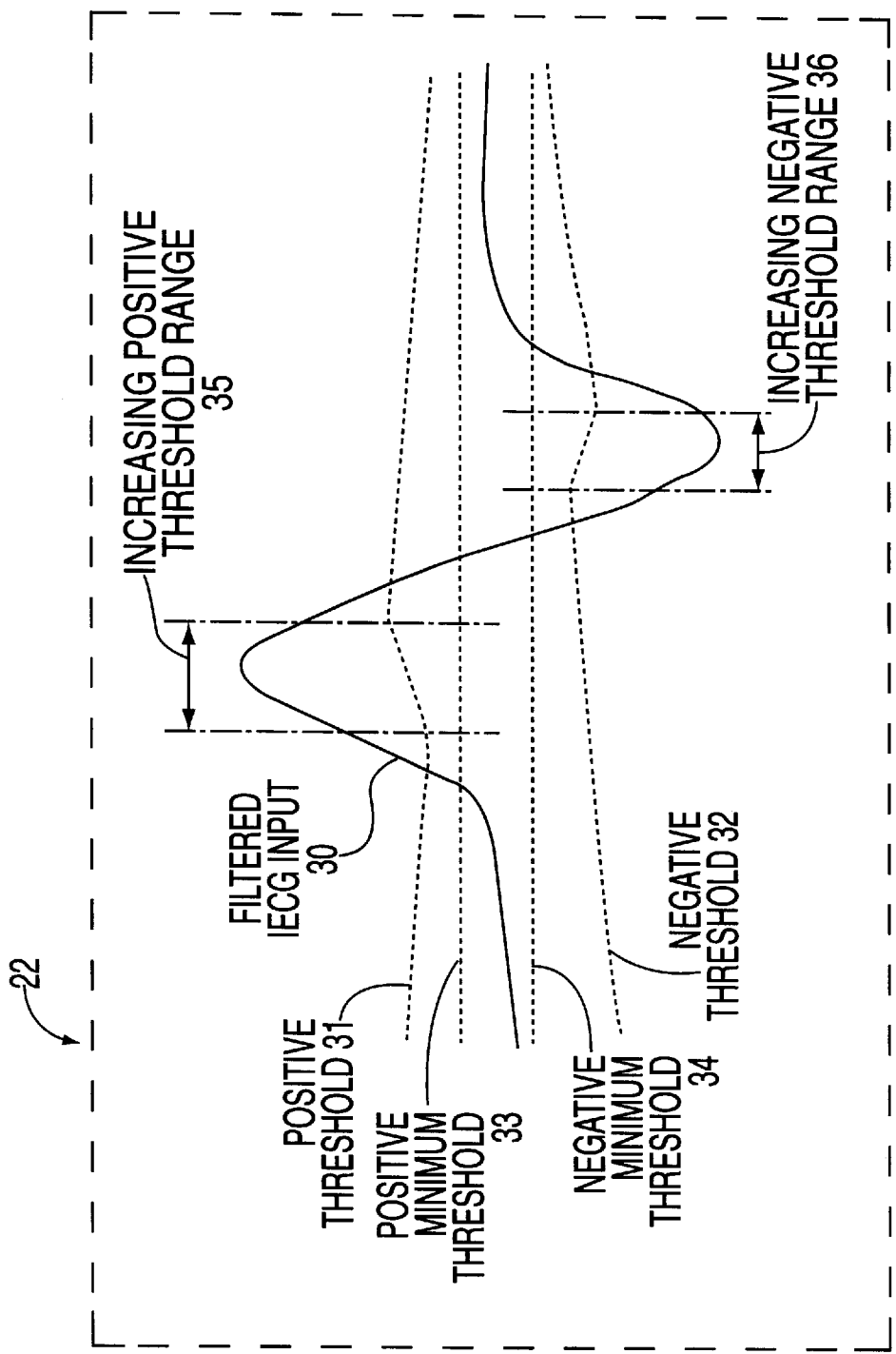
FIG. 3 shows a graph illustrating the behavior of the two dynamic thresholds derived in the apparatus of FIGS. 1 and 2.

Details of the detector 22 are found in U.S. Pat. No. 5,395,393 incorporated herein by reference. Briefly, as shown in FIG. 3, according to this patent, when the positive threshold 31 is greater than half the input signal 30, the threshold 31 decays exponentially towards the positive threshold minimum 33 with a time constant of approximately 0.75 seconds. When the positive threshold 31 is less than half the input signal 30, the positive threshold 31 follows up to half the input signal with a shorter time constant of 0.05 secs. The +Raw-sense output is digital signal generated whenever the input signal 30 exceeds the positive threshold 31.

The operation of the negative threshold 32 is a mirror image of that of the positive threshold 31.

Both thresholds have upper limits in that the positive threshold 31 cannot exceed a maximum value (in the preferred embodiment this value is 10 to 20 times the minimum threshold 33), and similarly, the negative threshold 32 cannot exceed a maximum (absolute) value related to the minimum negative threshold 34. In FIG. 3, curve 30 is shown without any noise components.

Figure 4A:
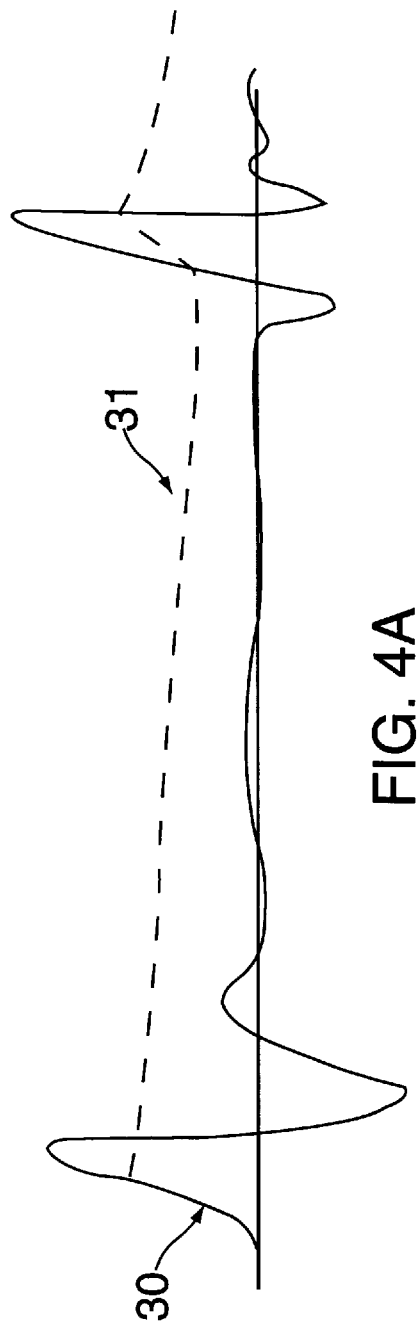
FIGS. 4A and 4B show graphs illustrating an IECG signal with and without noise.
Figure 4B:
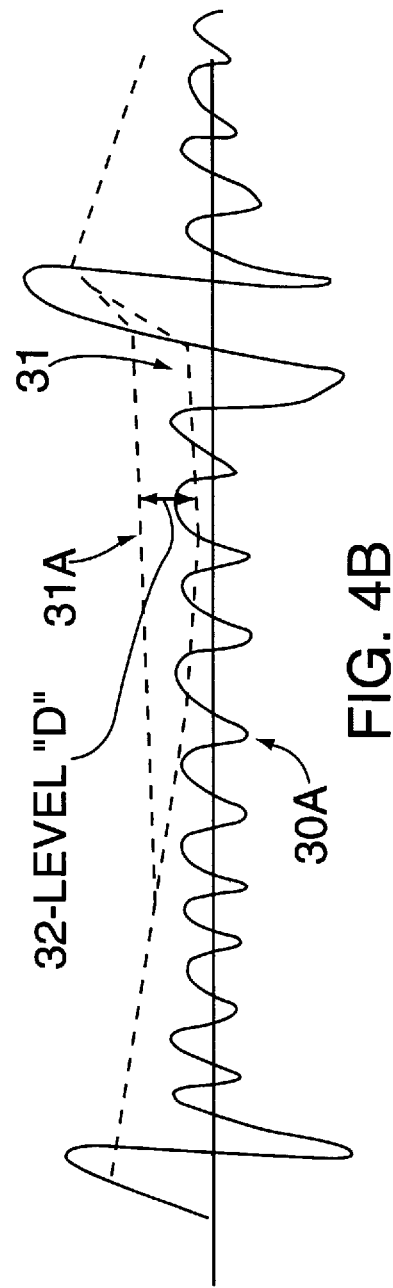

FIGS. 4A and 4B shows curve 30 (without the noise component) and curve 30A (with a noise component) respectively during a time frame following the one in FIG. 3. In this FIG. 3, the filtered IECG input 30 is well within the range deferred by 31 and 32. However, because curve 30A has a sinusoidal noise component as indicated, it is not contained by this range but it exceeds at least the positive threshold 31. If the noise has a large enough amplitude, it will probably also exceed the associated negative threshold as well. This problem is resolved by this invention by increasing the positive threshold 31A by level D (32), so that new threshold curve 31A is generated defined by

31A=31+D.

Preferably, D is selected so that it is equal to the peak amplitude N of the noise and an offset O. The offset provides a safety margin. In other words

D=N+O.

Preferably, O is about 20% of the threshold.

Referring to FIG. 2, the noise level N is detected by noise level detector 40. A threshold value detection circuit 49 is used to detect offset O. A summer 48 is then used to add N and O.

Figure 7:
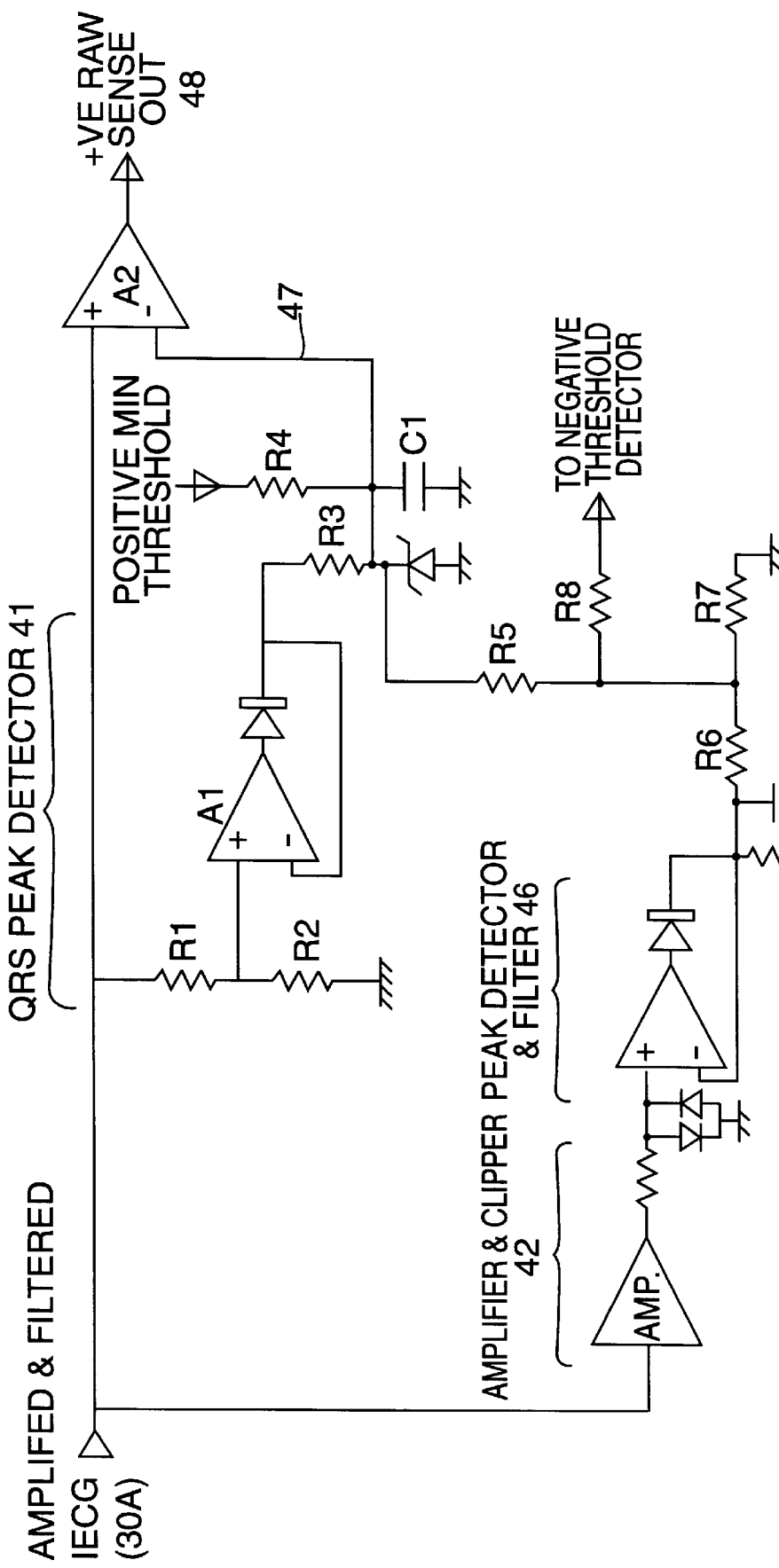
FIG. 7 shows details of the block diagram for the dynamic threshold calculator.

The negative threshold may also be decreased by amount D to insure that a negative excursion of 30A does not get interpreted erroneously as a cardiac signal. An implementation of these elements is shown in FIG. 7 and described in more detail below.

Figure 5:
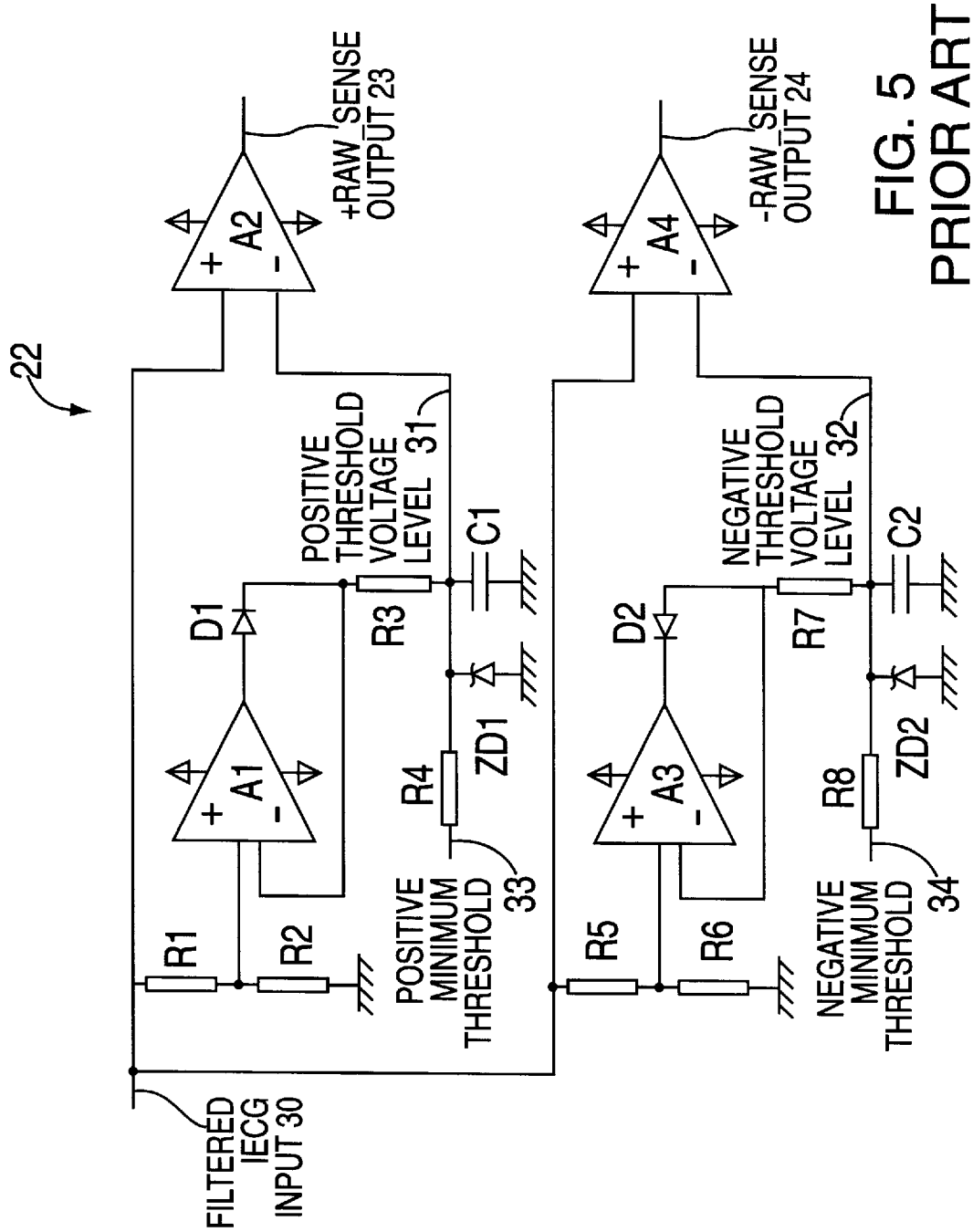
FIG. 5 shows details of a prior art circuit to implement the two dynamic thresholds.

Referring to FIG. 5, details of circuit 22 as depicted in U.S. Pat. No. 5,395,393 are shown to implement the dual dynamic threshold function. The positive threshold 31 is stored by capacitor C1. When the input 30 exceeds this voltage, the output of amplifier A2 goes high to output a +Raw-sense 41. When half the input voltage is less than the threshold +ve, the voltage on C1 is discharged exponentially through R4 towards +Thresh min. 33, a voltage which sets the minimum threshold. Resistors R1 and R2 provide half the input voltage of signal 30 to the precision rectifier formed by A1 and D1. When half the input voltage 30 exceeds the voltage +ve on C1, capacitor C1 is charged up to this new value through resistor R3 with a time constant of 0.05 secs.

The −Raw-sense output 44 is provided by a mirror image arrangement of the above circuit consisting of amplifiers A3 and A4 and associated components.

Figure 6:
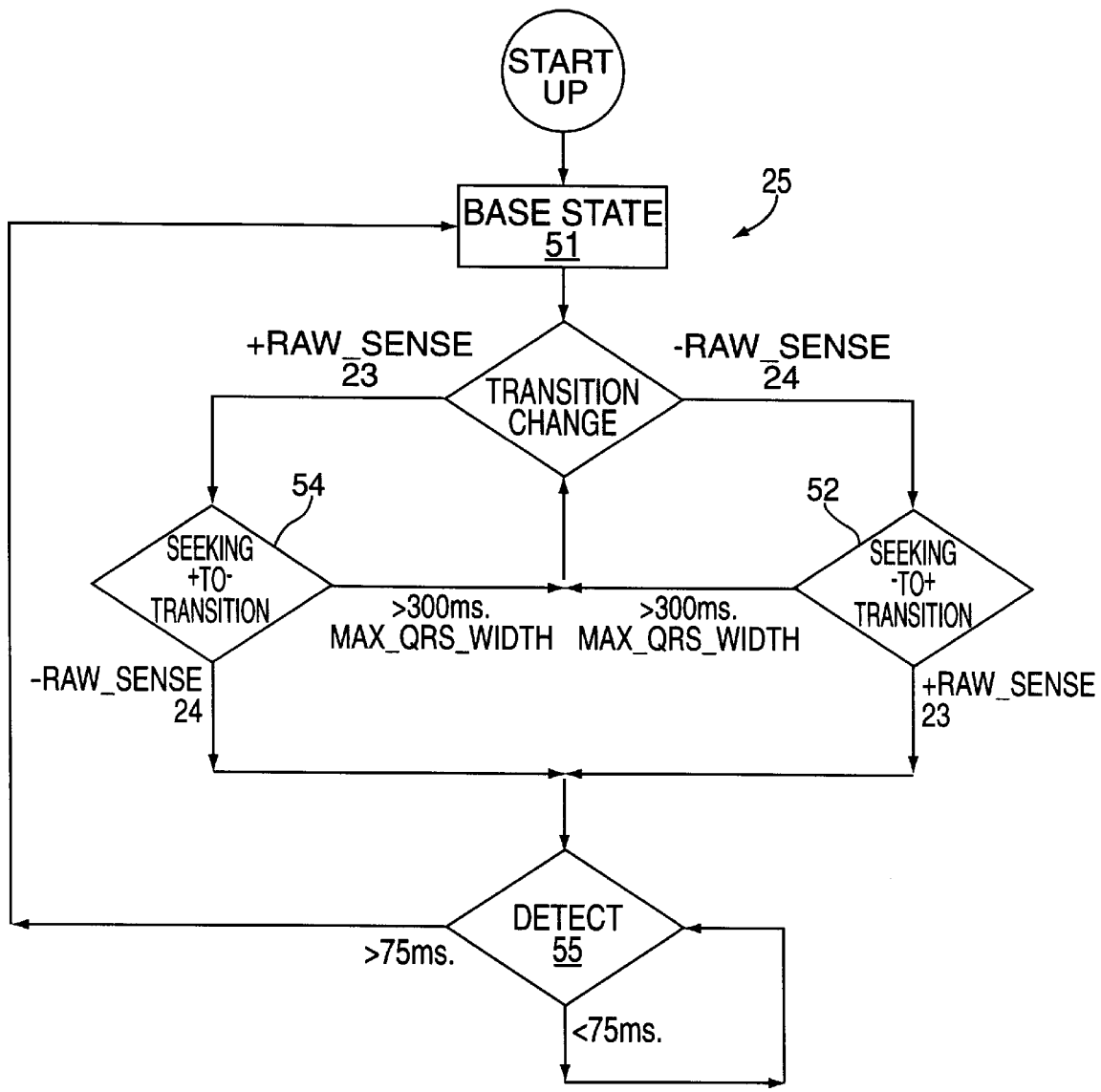
FIG. 6 shows a prior art flow chart of a state transition diagram for the clustering state machine.

Referring to FIG. 6, there is depicted the operation of the clustering state machine 25 in FIG. 2 in state transition diagram format. On start up, the state machine 25 commences operation in the base state 51. If a −Raw-detect is received from the dual threshold detector 22, the state machine 25 changes to the seeking − to + transition state 52. If a +Raw-detect signal is received, the state machine 25 changes to the seeking + to − transition state 54. If the state machine 25 spends more than 300 ms in either the seeking − to + transition or seeking + to − transition states, the state machine reverts to the base state 51.

If the state machine 25 is seeking − to + transition state 52 and a +Raw-detect is received, the state machine 25 will change to the detect state 55 and at this point, a valid-sense output 26 is generated. This signal indicates to the controller 15 that the QRS complex has been recognized by the sensing system 13 as a proper signal and can be processed to generate therapy for the heart (if any is required).

Similarly, if the state machine is seeking + to − transition state 54 and a −Raw-detect is received, the state machine 25 changes to the detect state 55 and generates a valid-sense signal 26.

The state machine 25 remains in the detect state 55 for 75 ms then reverts to the base state 51.

An important feature of the state machine 25 is that valid-sense signal 26 generated by a transition from triggering one threshold to the other threshold within a time window, which is in the range of about 300 ms.

The advantage gained by the clustering state machine is that with the filters described, large T waves often cause raw senses but are unlikely to generate two raw senses of opposite polarities within 300 ms as the majority of T waves have a duration of greater than 300 ms.

The clustering state machine 25 can be implemented by using discrete electronic logic or as a computer program that can be part of the controller 15 for the implantable defibrillator in FIG. 1.

As previously mentioned, the present invention modifies the arrangement of FIG. 5 to dynamically compensate for noise. More specifically, as seen in FIG. 2, a noise level detect circuit 40 is provided. This circuit 40 is shown in FIG. 7 together with the portion of the detection circuit 22 relevant to the detector of the positive signal +raw sense output. Circuit 40 consists of a clipper 42, diode 44, peak detector 46 and summing amplifier 48.

The circuit of FIG. 7 operates as follows.

The raw signal (30A) is fed to the QRS peak detector (41) which measures the peak amplitude of the QRS complex as described in FIG. 5.

This signal is also fed to a clipper 42. The clipper clips off the amplitude of the IECG signal 30A above 5 mv. In this manner most of the signal 30A is cut off to insure that the high amplitude components of IECG signal (such as the QRS complex) do not affect the noise measurements. The output of the clipper 42 is connected to a peak detector (46), the output of which is scaled by voltage divider R6 and R7 to form the level 'D' shown in FIG. 4.

This signal is added via R5 to C1 which holds the current positive threshold, where the minimum threshold is set by the input to R4. The values of R4, R5, R6 and R7 are proportioned such that the correct calculation of threshold being equal to 'D+O' as mentioned in FIG. 4 is achieved.

The resulting threshold signal on C1 (47) is then used as a reference for comparator A2. In this manner, the comparator A2 compares the signal 30A to the dynamically adjusted threshold D. Moreover, since this threshold D is adjusted automatically to the peak value of the noise, the output +RAW SENSE (48) is indicative of the signal IECG even in the presence of noise.

The RAW SENSE-output may be corrected by a similar circuit with reversed polarities. As the noise is most probably symmetrical, the output of this peak-detector can be used for the negative threshold circuit via R8.

The invention has been described herein in conjunction with a specific threshold variation scheme. Obviously, the same principles may be used to compensate for noise in conjunction with other threshold adjustment schemes. Alternatively, the thresholds may be programmed or preset to particular values and adjusted dynamically only for noise compensation.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

I claim:

1. An implantable cardiac device comprising:
    a sensor sensing intrinsic cardiac activity and generating a corresponding sensed signal, said sensed signal including a noise component having a peak noise amplitude;
    a pulse generator generating pulses in response to commands, said pulses being selected to provide cardiac therapy;
    a signal analyzer analyzing said sensed signal to generate an output signal indicative of a relation between said sensed signal and a threshold signal;
    a threshold signal generator for generating said threshold signal, said threshold signal having a threshold amplitude at least equal to said peak noise amplitude; and
    a controller receiving said output signal and generating in response said commands.

2. The device of claim 1 wherein said threshold signal generator includes a feature extractor extracting said peak noise amplitude of said noise component.

3. The device of claim 1 wherein said signal analyzer is a comparator comparing said sensed signal to said threshold signal.

4. The device of claim 3 wherein said threshold generator includes an amplitude detector for detecting said peak noise amplitude.

5. The device of claim 4 wherein said threshold signal generator includes a fractional sensor for generating a fractional signal indicative of a preselected fraction of said sensed signal, and wherein said threshold signal is dependent on said fractional signal.

6. An implantable cardiac device comprising:

a sensor sensing intrinsic cardiac activity in a cardiac chamber and generating a corresponding sensed signal, said sensed signals including a noise component with a peak noise amplitude;

a pulse generator generating pulses in response to commands, said pulses being structured to provide a therapy selected from antibradycardia, antitachycardia, cardioversion and defibrillation;

an analyzer analyzing said sensed signal in comparison to a threshold signal and generating a corresponding analyzed signal;

a threshold signal generator generating said threshold signal, said threshold signal including a first part which is varied dynamically in accordance with a preset criteria and a second part which is at least equal to said peak noise amplitude; and a controller receiving said analyzed signal and generating in response said commands.

7. The device of claim 6 wherein said threshold signal generator includes a feature extractor for extracting said peak noise amplitude.

8. The device of claim 6 wherein said threshold signal generator further includes a clipper for clipping a portion of said sensed signal before said peak amplitude is extracted.

9. The device of claim 6 wherein said threshold signal generator includes a summer for summing said first and second parts.

10. The device of claim 6 wherein said threshold signal generator further includes an offset signal generator for generating an offset signal selected to supply a safety margin, and wherein said threshold signal generator includes a summer for summing said first and second parts and said offset signal.

11. The device of claim 6 wherein said sensed signal includes a cardiac component and said noise component, and wherein said threshold signal generator includes a detector for detecting an amplitude of said cardiac component, said generator generating said first part as a fraction of said amplitude.

12. The device of claim 11 wherein said cardiac component is a biphasic signal and wherein said first threshold part includes a positive threshold signal and a negative threshold signal.

* * * * *